United States Patent

Fareed

[11] Patent Number: 6,077,241
[45] Date of Patent: Jun. 20, 2000

[54] FOREARM TRANSAXIAL COMPRESSION BAND

[76] Inventor: Donald O. Fareed, 801 Buena Vista Ave., Santa Barbara, Calif. 93108

[21] Appl. No.: 08/667,378

[22] Filed: Jun. 21, 1996

Related U.S. Application Data

[63] Continuation-in-part of application No. 08/424,877, Apr. 19, 1995, abandoned, which is a continuation of application No. 08/155,426, Nov. 19, 1993, abandoned, which is a division of application No. 07/976,646, Nov. 13, 1992, Pat. No. 5,295,951, which is a continuation of application No. 07/806,863, Dec. 12, 1991, abandoned, which is a continuation of application No. 07/744,871, Aug. 14, 1991, Pat. No. 5,152,302.

[51] Int. Cl.[7] .................................................. A61F 13/00
[52] U.S. Cl. ................................ 602/62; 602/20; 2/16; 473/63
[58] Field of Search ................................ 602/5, 21, 12, 602/66, 25, 20, 62, 63; 128/878, 880, 881, 882, DIG. 15; 273/29 R; 2/16; 473/63

[56] References Cited

U.S. PATENT DOCUMENTS

| | | | |
|---|---|---|---|
| 34,112 | 1/1862 | Lambert | 606/203 |
| 1,623,125 | 4/1927 | Levine | 128/881 |
| 2,318,864 | 5/1943 | Jackson | 602/21 |
| 3,074,723 | 1/1963 | Esty | 128/881 |
| 3,827,107 | 8/1974 | Moore | 128/DIG. 15 |
| 3,970,081 | 7/1976 | Applegate, Jr. | 128/95 |
| 4,191,373 | 3/1980 | Lancellotti | 273/29 A |
| 4,427,007 | 1/1984 | Rexroth | 128/105.1 |
| 4,436,088 | 3/1984 | Finnieston | 128/878 |
| 4,576,150 | 3/1986 | Auracher | 128/DIG. 15 |
| 4,628,918 | 12/1986 | Johnson, Jr. | 128/90 |
| 4,763,901 | 8/1988 | Richter | 602/20 |
| 4,796,611 | 1/1989 | Wardlaw | 602/12 |
| 4,905,998 | 3/1990 | Last | 273/29 |
| 4,966,137 | 10/1990 | Davini | 128/878 |
| 5,286,249 | 2/1994 | Thibodaux | 602/5 |
| 5,339,834 | 8/1994 | Marcelli | 128/878 |
| 5,385,537 | 1/1995 | Davini | 602/21 |
| 5,520,619 | 5/1996 | Martin | 602/5 |

FOREIGN PATENT DOCUMENTS 20744452  11/1981  United Kingdom ............ 128/881

OTHER PUBLICATIONS

Elbow Shock Absorber, Hammacher Schemer Catalog, Summer 1983.

*Primary Examiner*—Danton D. DeMille
*Assistant Examiner*—Justine R. Yu
*Attorney, Agent, or Firm*—Joseph L. Strabala

[57] ABSTRACT

A device adapted to be circumferentially fitted around the forearm to alleviate symptoms of overuse injuries, such as tennis elbow. The device is an elongate band composed of two elongate arcuate compression plates detachably and adjustably linked end to end by flexible straps. Each of the compression plates has an inwardly concave skin contacting surface which, in operation, are in circumferent opposition on the forearm to compress the skin overlying the radial extensor and flexor muscles within the forearm transaxially disposed therebetween. When the band is circumferentially tensioned and fastened to encircle the forearm, only the discrete, anatomically opposed skin contacting surfaces of the compression plates press against the skin. The skin contacting surfaces of the two compression plates are positioned by the user to immediately overlie the extensor and flexor muscle mass respectively. Only the skin underlying the skin-contacting surface of the compression plates and the intervening tissue transaxially disposed therebetween is compressed. Other circumferential portions of the forearm underlying the band are not compressed and the venous blood return is substantially unimpaired by the band.

7 Claims, 3 Drawing Sheets

FOREARM TRANSAXIAL COMPRESSION BAND

CROSS-REFERENCE TO RELATED APPLICATIONS

This is a continuation-in-part of U.S. Ser. No. 08/424,877, filed Apr. 19, 1995, now abandoned which is a continuation of U.S. Ser. No. 08/155,426, filed Nov. 19, 1993, now abandoned which is a divisional of U.S. Ser. No. 07/976,646, filed Nov. 13, 1992, now U.S. Pat. No. 5,295,951, which is a continuation of U.S. Ser. No. 07/806,863, filed Dec. 12, 1991, now abandoned which is a continuation of U.S. Ser. No. 07/744,871, filed Aug. 14, 1991, now U.S. Pat. No. 5,152,302.

FIELD OF THE INVENTION

The present invention relates generally to an adjustable compression arm band and, more specifically, to an arm band constructed to be worn by persons suffering from symptoms of lateral epicondylitis (tennis elbow), radial supinator syndrome and medial epicondylitis.

PRIOR ART

Tennis elbow, sometimes referred to in the prior art alternatively as lateral epicondylitis or epicondylalgia externa, commonly encountered in men and women between the ages of thirty and fifty who engage in racket sports. In people in the aforesaid age group, muscles and tendons become less supple and less able to absorb and dissipate the forces associated with sudden acceleration and deceleration of muscle groups within the forearm which cause the inflammation associated with tennis elbow, particularly where the extensor muscle mass meets the bone. Tennis elbow is also found in individuals pursuing activities such as golf and bowling. It is also found in certain trades such as carpentry, due to repeated hammering and driving of screws, and house painting, due to the forward and backward stroke of the brush.

Although "tennis elbow" is frequently thought of as an inflammation of the extensor muscles of the forearm, such inflammation may be accompanied by radial supinator inflammation due to repetitive pronation and supination. Such inflammation of the supinator muscle mass can cause tension on the overlying extensor muscle and resultant inflammation. The forearm extensor and supinator muscles are those that come into play during the extension, raising or snapping of the wrist. Every time a tennis ball hits a racket, there is a certain force or mechanical shock wave propagated up the forearm muscles which are already in tension due to the weight and acceleration of the racket and the tension caused by the centrifugal force of the stroke. If the ball is mis-hit, an extra force is added resulting In a snap of the wrist. It is this extra repetitive stress that causes the trauma leading to inflammation in the extensor and supinator muscles.

Prior art devices and procedures to control "tennis elbow" have been principally directed to lateral epicondylitis due to inflammation of the extensor muscle mass. Such devices include tension bandages for support and non-elastic bandages which are fastened around the forearm to inhibit the massive movement of the extensor and flexor muscles and absorb much of the shock. The following United States patents describe such devices and are made of record: U.S. Pat. Nos. 4,628,918; 4,905,998; 3,970,081; and 4,191,373.

Applegate, Jr., in U.S. Pat. No. 3,970,081 (referenced above) describes a support to be worn on the arm near the elbow joint for reducing pain in the elbow joint associated with the condition of tennis elbow. Applegate, Jr.'s strap comprises a tubular sleeve of one-way stretch fabric with an integral non-elastic strap. In use, the tubular sleeve is pulled up over the arm and positioned. The strap is tightened to compress a disc housed thereunder causing the disc to press against the forearm. Applegate, Jr. teaches positioning the tubular sleeve such that the compression disc underlying the inelastic band may be positioned on the arm wherever it will provide or afford the most relief. The Applegate, Jr. sleeve and integral band is substantially circular and because it is circular, it applies pressure substantially evenly about the forearm thereby impairing the circulation much like a tourniquet. It is, therefore, desirable to provide a pressure band similar to Applegate, Jr.'s without the disadvantage of impairing blood circulation in the forearm.

Each of the aforesaid patents provides for a device to relieve the symptoms of lateral epicondylitis. Each of the devices stresses either absorption of shock and vibration or the application of warmth or heat and pressure. None of the devices addresses the associated problems of flexor and supinator muscle inflammation or the problem of impeded blood circulation due to compression of non-target tissues in the forearm or upper arm. It is, therefore, desirable to provide a compression band useful for treating the symptoms of tennis elbow whether due to extensor, flexor or supinator inflammation. Additionally, the design of the band should minimally impair normal circulation up and down the arm.

SUMMARY OF THE INVENTION

The invention provides an adjustable band adapted to be worn on the forearm athlete or someone suffering from the symptoms of overuse injuries such as tennis elbow comprising a means for applying transaxial pressure selectively to the extensor, flexor and supinator muscles of the forearm and, at the same time, not substantially compressing non-target tissues of the forearm. In this regard, it is helpful to consider the cross-sectional geometry of the forearm. In cross-section, the forearm is not round, it is elliptical. A circular compression strap (such as those described in the prior art) placed around the forearm will compress the greater diameter of the ellipse more than other areas of the circumference. In other words, a circular strap provides the greatest compression at the greatest diameter of the ellipse. Depending on the anatomy of the individual, the portions of the forearm circumference at the greatest diameter may not overlie the inflamed muscle masses associated with tennis elbow. Such a prior art band would merely function as a tourniquet to impede blood flow up the arm. It is, therefore, an object of this invention to provide a compression band to be worn on the forearm and adapted to adjustably apply transaxial compression selectively to the flexor, extensor and supinator muscle masses in the forearm without substantially compressing non-target tissues.

It is still another object of this invention to provide a compression band for use around the forearm comprising an inelastic eccentric strap with discrete, elastic inwardly protruding means on the forearm-contacting surface of the strap for selectively pressing against the flexor and extensor muscles.

Another object of this invention is to provide a forearm compression band with means on the inner surface thereof for selectively applying transaxial countercompression against an anatomically opposed pair of target tissues such as the extensor and flexor muscle wad where said countercompression means may be easily adjusted by the user while in use.

DESCRIPTION OF THE PREFERRED EMBODIMENT

Figure 1:
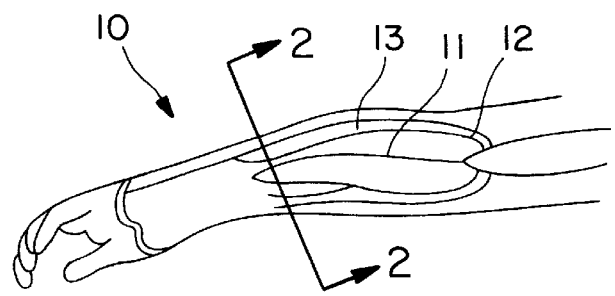
FIG. 1 is a longitudinal cutaway section of a forearm showing the extensor and flexor muscles and epicondyle.

FIG. 1 is a cutaway view of the forearm generally indicated at 10 showing the extensor carpi radialis brevis muscle wad 11 and the extensor carpi radialis brevis muscle wad 13. The lateral epicondyle is indicated at the numeral 12. The extensor radialis muscle groups 11 and 13 "or wads" are elongate more or less sausage shaped muscles enclosed in a fascia.

Figure 2:
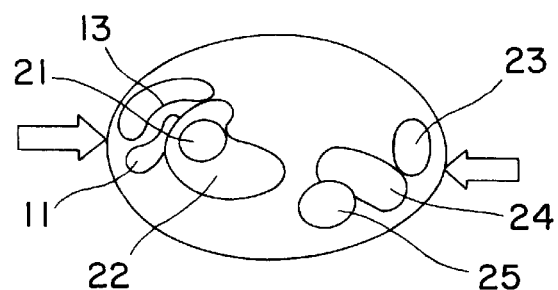
FIG. 2 is a transverse cross-sectional view of the forearm along line 2—2 of FIG. I showing the extensor, flexor and supinator muscle wads.

The cross-section of the sausage-shaped flexor and extensor muscles is shown in FIG. 2. The radial supinator complex 22 surrounds the radius 21 and directly underlies the extensor muscles 11 and 13. As used herein, the term "transaxial compression" or alternatively, "transaxial countercompression," refers to opposing pressure applied across the forearm in the general direction of the two broad arrows. Transaxial compression is similar to placing a forefinger over the extensor muscle of the forearm and a thumb over the flexor muscle and pinching. It is seen that such transaxial countercompression will simultaneously compress the extensor muscles 11, 13 and the underlying supinator muscle 22 and the opposing flexor muscles 23 and 24 adjacent to the ulna 25.

Figure 3A:
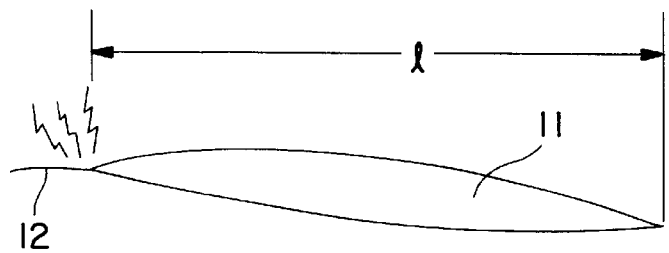
FIG. 3A is a schematic view of an inflamed muscle and epicondyle in a rest position.
Figure 3B:
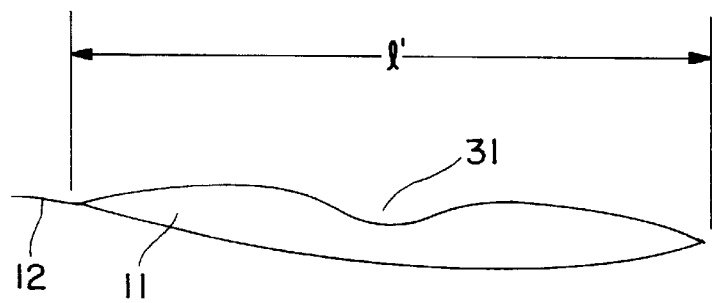
FIG. 3B is a schematic view of the muscle of 3A showing the increase in length resulting from an applied pressure.

Turning now to FIG. 3A and B, an inflamed arbitrary muscle, for example, the extensor carpi radialis brevis "wad" is shown. FIG. 3A depicts the wad under tension having tenderness resulting from inflammation of the muscle near its point of insertion on the lateral epicondyle 12. The tenderness is aggravated by tension on the wad as occurs during movement of the wrist. In such a case, the length of the wad is shortened causing stretching of the wad at the lateral epicondyle and pain. In FIG. 3B, the wad is compressed at a point 31 along its length. Since the wad is enclosed in a fascia and is substantially noncompressible, the compression causes the muscle wads resting length l to increase to a new length l' where l' is greater than l. Lengthening the muscle wad generates slack therein and relieves the tension at the point of insertion with concomitant relief of the associated pain.

It is important to note that the forearm is substantially elliptical in cross section. A circular band applied to the forearm for the purpose of applying pressure to the wad will preferentially apply pressure at the greatest diameter of the ellipse thereby compressing the underlying blood vessels and impeding blood circulation. It is, therefore, desirable to provide the encircling portion of the compression band with an asymmetry such that only the flexor, supinator and extensor muscles are substantially compressed by the band.

Figure 4:
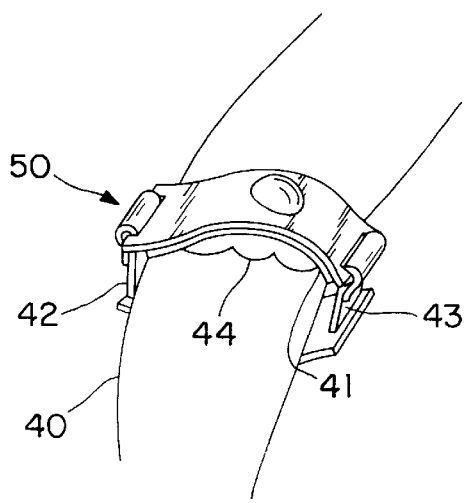
FIG. 4 is a view of the transaxial compression arm band showing the arm band circumferentially positioned about an arm.
Figure 5:
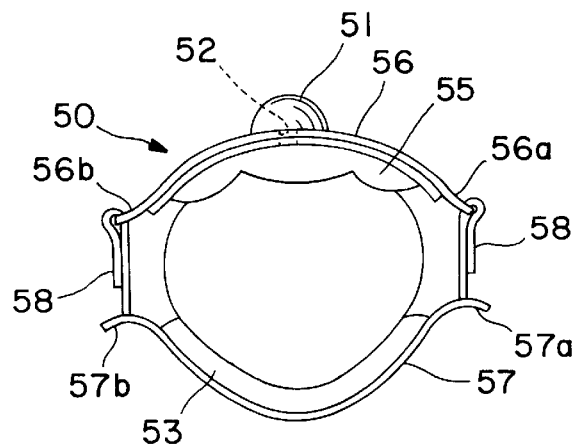
FIG. 5 is a front view of the arm band of FIG. 4.
Figure 6:
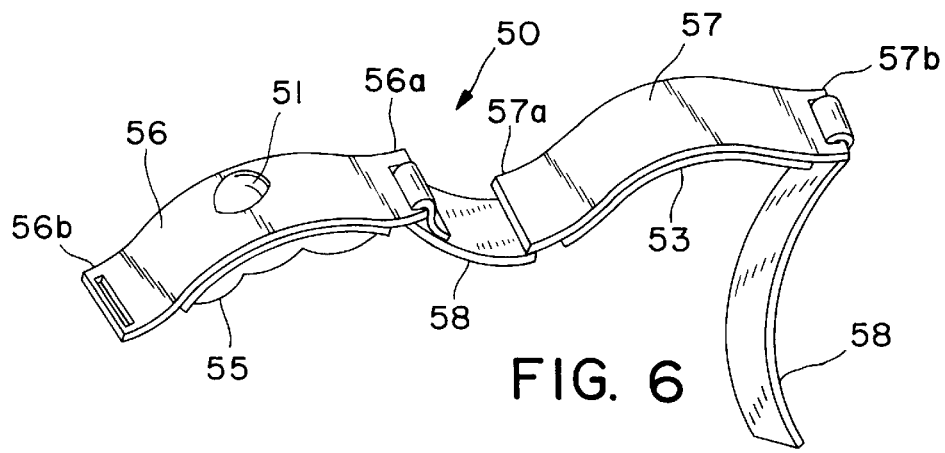
FIG. 6 is a perspective view of the transaxial compression band of the present invention.

Such an asymmetry is shown generally in FIG. 4 and in more detail in the preferred embodiment shown in FIG. 5. In FIG. 4, a band 50 is shown encircling the forearm 40. The band 50 has inner skin contacting surfaces 41 with discontinuities at 42 and 43. The positions of the discontinuities are such that they overly the non-target tissues to minimize pressure thereon. When in use, the encircling band may be positioned about the forearm to align the discontinuities 42 and 43 to overlie the non-target tissues of the forearm. The two opposing protuberances 44 (only one is shown in FIG. 4) may then be positioned to overly the extensor and flexor wad and the band tightened. The presence of a plurality of discontinuities about the inner circumference of the band will enable unrestricted circulation of the blood and enable compression of a selected muscle group.

A particularly preferred embodiment of a compression band according to the teachings of the invention is shown in FIG. 5. The band, generally indicated at 50, has a skin contacting pad 53 and at least one inflatable balloon-like skin-contacting member 55 disposed on its inner surface. A pump 51, which preferably may be operated by finger pressure, is mounted on the outer surface of the band. The pump 51 is in fluid communication with the interior of the inflatable member by means of a channel 52 permitting adjustment to provide the desired pressure against the underlying muscle group.

The construction of the band 50 is specially adopted to provide transaxial countercompression. The band 50 comprises two substantially "U" shaped inelastic plates: an upper plate 56 and a lower plate 57 linked to one another by one or more adjustable straps 58. In the preferred embodiment, the inner skin contacting surface of the upper plate 56 comprises one or more inflatable elastomer balloons 55, the pressure within the interior chamber of the balloons being adjustable by means of a finger-activated pump/exhaust 51. The skin contacting surface of the lower plate 57 is conveniently lined with a closed cell foam 53 for comfort. When the strap 50 is securely fastened around the forearm with the opposing skin-contacting surfaces 53 and 55 overlying the extensor and flexor muscles, inflation of the balloon(s) 55 by means of the pump 51 draws the lower plate 57 toward the upper plate 56 thereby providing transaxial countercompression of the flexor, supinator and extensor muscles.

Figure 7:
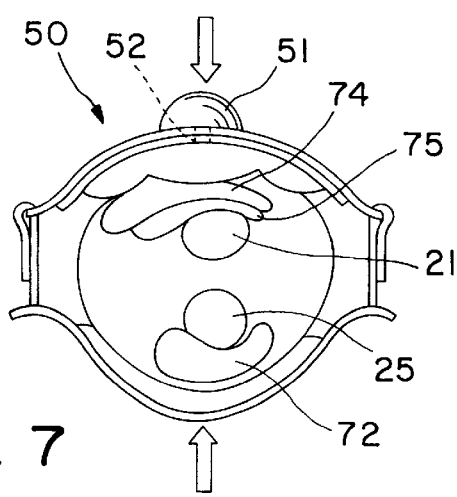
FIG. 7 is a cross-sectional view of the transaxial compression band around the forearm.

The transaxial compression is seen more clearly in FIG. 7. The flexor muscle mass 72 is located adjacent to the ulna 25. The extensor muscle mass 74 lies adjacent to the supinator complex 75 which, in turn, lies adjacent to the radius 21. It is clear that counter compression of the upper and lower plates in the direction of the heavy arrows will compress the flexor, extensor and supinator muscles.

As mentioned earlier, an advantage of using the present transaxial compression band is that it is useful for treating medial epicondylitis and radial supinator syndrome as well as lateral epicondylitis. Even if the patient does not have these complaints, the band will have little adverse effect on circulation. Prior art devices rely on tightening a strap to apply significant compression deep to the muscle. Such pressure causes the veins to distend and impedes circulation. The transaxial compression band minimizes the tourniquet effect. In addition, If the underlying tissue is inflamed, holding transaxial compression on the muscles during exercise helps squeeze fluids from the inflamed tissue and mechanically decrease the associated swelling.

Figure 8:
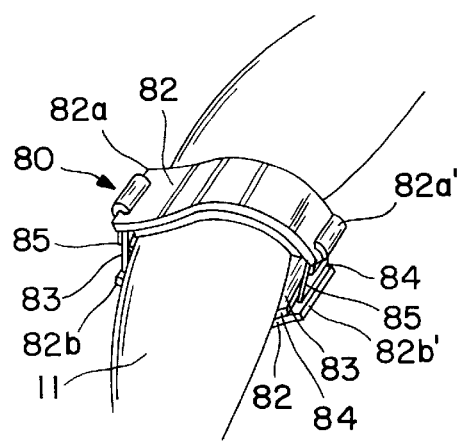
FIG. 8 is a perspective view of a non-adjustable embodiment of a transaxial compression band circumferentially attached to the forearm of a person.
Figure 9:
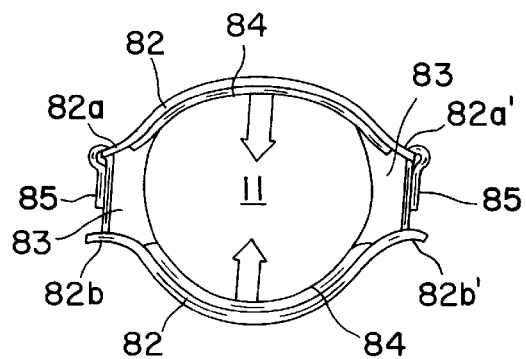
FIG. 9 is a front end-on view of the band of FIG. 8 encircling the forearm of a person.

In FIG. 8, a band 80 is shown encircling a forearm 11. The band 80 comprises two compression plates 82 having concave inner skin-contacting surfaces 84 being linked together by two flexible plate connectors 85 with the concave inner surfaces 84 facing one another. The lateral outermost ends 82a and 82b and 82a and 82a of the compression plates 82 are recurved, projecting upward, away from the skin-contacting surface 84 and forming lugs at the upper surface which elevate and space the flexible connectors 85 from the underlying skin by a gap as shown at 83. A description of only one of two identical structural features is meant to also apply to the mating identical element. The gaps 83 are circumferentially disposed around the band so that they overly non-target tissue to permit relatively unimpeded axial venous return of blood through the forearm. When the band 80 is attached to encircle the forearm the band is rotated until the two opposing compression plates 82 overlie the transaxial portion of the extensor and flexor muscles respectively with the gaps 83 overlying the non-target tissues of the forearm. The length of one of the flexible connectors 85 is circumferentially adjusted to optimize transaxial compression. FIG. 9 is an end-on view of the band of FIG. 8 showing the countercompressive forces, indicated by the axially directed broad arrows, exerted on the circumscribed transaxially disposed underlying tissue by the compression plates 82.

Figure 10:
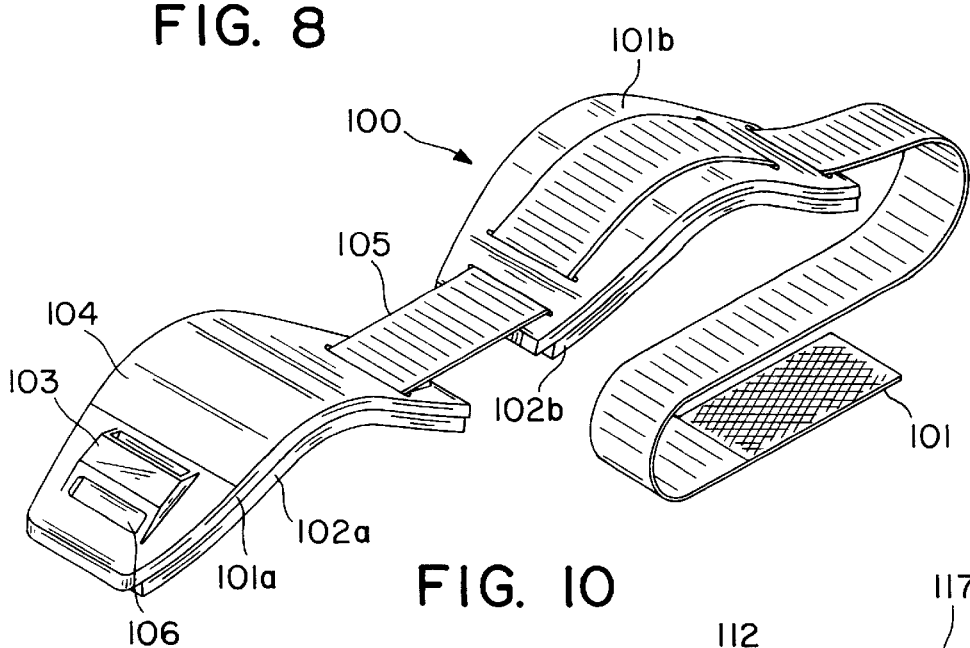
FIG. 10 is a perspective view of a particularly preferred embodiment of a transaxial compression band employing an adjustable strap for changing transaxial compression exerted by the band.

A further embodiment of a transaxial compression band shown at 100 in FIG. 10. The band 100 has opposed compressed plates 101a and 101b, each having a flexible, compressible skin-contacting liner 102a and 102b disposed on the inner skin-facing surface of the respective plates. The band 100 comprises two independent substantially arcuate, slightly flexible plates 101a and 101b linked end-to-end at the lateral extensions thereof by an adjustable strap 105. The flexible plates 101a and 101b, while supple, are relatively inelastic in comparison with the liners, but are capable flexing as the skin-facing surface of the compression plate conforms, under pressure, to an adjacent anatomically contoured surface. The skin-facing surfaces 102a and 102b of the compression plates 101a and 101b are covered with skin-contacting liners, such as a closed-cell foam, for comfort. When the band 100 is placed on the forearm of a user with a compression plate positioned over the extensor muscles, the free-end 107 of the strap 105 is passed through the slot 106 on the lug 103, and the skin-facing surfaces 102a and 102b of the compression plates 101a and 101b are drawn together by manually applying tension on the free-end 107 of the strap to compress the portion of the underlying muscle groups transaxially disposed between the plates.

When a transaxial compression band is accordance with the present invention is positioned on the forearm, the lateral extension of a volume of intervening tissue is bounded by the transaxially opposing compression plate. The bounded volume of tissue may be viewed as a column of tissue within the forearm, the column having a length equal to the distance between the compression plate, measured across the forearm, and the cross-sectional area of the tissue column being uniform and equal to the area of a skin-contacting surfaces of the opposed compression plates.

Figure 11:
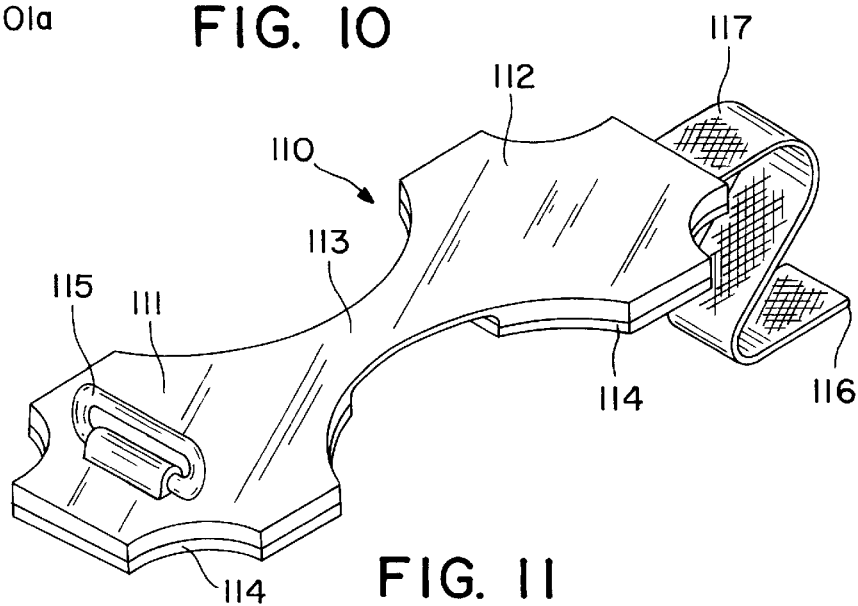
FIG. 11 is a perspective view of yet another embodiment of a transaxial compression band wherein the flexible compression plates are opposing ends of an elongate unitary member and are spaced from one another and interconnected by a narrow flexible waist portion therebetween.

The essential feature of the device of the present invention is providing a user with a mountable device which can exert inwardly directed pressure to discrete anatomically opposed areas of the forearm to compress a column of tissue disposed between the two plates. The band is constructed so that in use, the flexible plate-connecting linkages do not press upon the underlying skin. This feature provides a band that enables venous blood return during use. These features are provided by a third preferred embodiment of a transaxial compression band 110 shown in FIG. 11 wherein the transaxial compression plates 111 and 112 are portions of a unitary sheet and connected to one another by a narrow, relatively thin, flexible central waist portion 113 and laterally disposed symmetrically with respect thereto. The compression plates 111 and 112 and the waist portion 113 are unitary, preferably formed in a mold with both the width and thickness of the central waist portion 113 being less than the width and thickness of the compression plates. The difference in thickness of the compression plates and the waist will depend upon the elevation of the flexible connectors required to produce a gap under the waist portion between the compression plates and the flexibility of the elastomer. Foam liners 114 affixed to the lower surface of the compression plates 111 and 112 provide comfort and conforming fit. A lug 115 disposed on the lateral portion of the upper surface of compression plate 111 provides means for connecting the free end 116 of strap 117 to the lateral portion of the compression plate 111 and for adjusting the transaxial compressive forces.

It is to be understood that numerous modifications may be made in the illustrated preferred embodiment and other arrangements may be devised without departing from the spirit and scope of the invention as set forth in the appended claims.

What I claim is:

1. A medical device adapted to encircle a person's arm for relieving symptoms of inflammatory conditions associated with overuse injured as tennis elbow without impeding the arm's range of motion or restricting venous return of blood from portions of a user's arm distal to the device, said device comprising:

two independent generally elongated compression plates, each of said compression plates having an arcuate central portion with its distal ends extending generally tangential from its arcuate central portion;

each of said arcuate portions of said compression plates having an elastomer liner attached to its inner concave surface, said liners being sufficiently extensive so as to overlay the flexor and extensor muscles of a user's forearm under said compression plates;

a first flexible strap means operably connecting together in a non-elastic relationship said distal end on one of said two independent compression plates with said distal end of said other of said two compression plates so that respective arcuate portions of said two independent compression plates are opposed to one another; and a second flexible strap means operably connecting together in a non-elastic relation said other distal end on one of said two independent compression plates with said other distal end of said other of said two compression plates so that respective portions of said two independent compression plates are opposed to one another, said second strap means being operable to adjustably connect and disconnect to one of said distal ends to which it is attached whereby the device can be placed on a user's forearm in an encircling relationship with said two compression plates overlaying portions of the flexor and extensor muscles respectively of a user's forearm and said strap means adjusted to apply pressure generally limited to discrete anatomically portions of a user's extensor and flexor muscles respectively without restricting the blood flow in a user's forearm.

2. The medical device defined in claim 1 wherein the first strap means is an inextensible fabric strap.

3. The medical device defined in claim 1 wherein the second strap means is an inextensible fabric strap.

4. The medical device defined in claim 1 wherein the first and second strap means are formed for a single inextensible fabric strap.

5. The medical device defined in claim 1 wherein the first and second strap means are both adjustable.

6. The medical device defined in claim 1 wherein the first and second strap means are formed of an inextensible member connected to the distal ends of the two compression plates.

7. The medical device defined in claim 1 wherein the two compression plates are sufficiently elastic so said plates are operable to deflect slightly when said strap means are adjusted on a user's arm.

* * * * *